United States Patent [19]
Trowell et al.

[11] Patent Number: 5,871,939
[45] Date of Patent: Feb. 16, 1999

[54] AGENTS AND METHOD FOR IDENTIFYING INSECTS

[75] Inventors: Stephen Charles Trowell, Oxley; Kim Astrid Garsia, O'Connor; Amanda Susan Hill, Cook, all of Australia; Gabriele Annierose Lang, Weilheim, Germany; John Howard Skerritt, Cook, Australia

[73] Assignee: Commonwealth Scientific and Industrial Research Organization, Campbell, Australia

[21] Appl. No.: 186,767

[22] Filed: Jan. 25, 1994

[30] Foreign Application Priority Data

| Jan. 26, 1993 | [AU] | Australia | 6943/93 |
| Jul. 26, 1993 | [AU] | Australia | 0164/93 |

[51] Int. Cl.⁶ .................................................. G01N 33/567
[52] U.S. Cl. ........................ 435/721; 435/79; 435/24.27; 435/90.21; 435/188; 436/533
[58] Field of Search .................................. 435/7.21, 7.9, 435/240.27, 70.21, 7.92, 188; 436/533, 525; 530/388.2, 388.24, 387.1, 388.25, 389.1, 389.2, 389.3, 391.1, 391.3

[56] References Cited

U.S. PATENT DOCUMENTS 5,118,610  6/1992  Kitto et al. ............................ 435/7.21

OTHER PUBLICATIONS

Marlow and Lane, "Digesting Antibodies with Papain to Isolate Fab Fragments", *Antibodies: A Laboratory Manual*, 15:628–631 (1988).

Schulz, K.F., et al., "Monoclonal Antibodies Specific for Apoproteins of Lipophorins From the Migratory Locust", *Archives of Insect Biochemistry and Physiology*, 6:97–107 (1987).

Stuart, M.K., et al., "Beyond ELISA: A Rapid, Sensitive, Specific Immunodot Assay for Identification of Predator Stomach Contents", *Annals of the Entomological Society of America*, 83:1102–1106 (1990).

Greenstone, M.H., et al., "Foreign Exploration for Predators: A Proposed New Methodology", *Environmental Entomology*, 18(2):195–200 (1989).

Greenstone, M.H., et al., "Predation on *Heliothis zea* (Lepidoptera: Noctuidae): An Instar–Specific ELISA Assay for Stomach Analysis", *Annals of the Entomological Society of America*, 82(1):45–49 (1989).

Lenz, C.J., Production of a Monoclonal Antibody to the Arylphorin of *Heliothis zea*, *Archives of Insect Biochemistry and Physiology*, 167–177 (1988).

Ryan, R.O., et al., "Chemical and Immunological Properties of Lipophorins From Seven Insect Orders", *Archives of Insect Biochemistry and Physiology* 1:375–383 (1984).

Trowell, S., et al., "A Monoclonal Antibody Kit to Distinguish *Helicoverpa armigera* from H Punctigera", *Divisional Report of Research*, 77 (1992).

Trowell, S., et al., "Development Trials of the Heliothis ID Kit", *Sixth Australian Cotton Conference*, 209–216 (1992).

"Heliothis Management in Cotton", *Entomology—Science For Survival*, (1990).

Trowell, S., et al., "The New Heliothis ID Kit Giving Chemicals a Better Chance", *CSIRO Australia*, Sep./Oct. 1991.

Trowell, S., et al., "A Heliothis Identification Kit", *Fifth Australian Cotton Conference*, 267–275 (1990).

Greenstone, M.H., et al., "Using Monoclonal Antibodies for Phylogenetic Analysis: An Example from the Heliothinae (Lepidoptera: Noctuidae)", *Annals of the Entomological Society of America*, 84(5):457–464 (1991).

Buchner, J., et al., "Renaturation, Purification and Characterization of Recombinant $F_{ab}$–Fragments Produced in *Escherichia coli*", *Bio/Technology*, 9:157–162 (1991).

Austin, P., et al., "Will dAbs challenge mAbs?", *Nature*, 341:484–485 (1989).

Ward, E.S., et al., "Binding activities of a Repertoire of Single Immunoglobulin Variable Domains Secreted from *Escherichia coli*", *Nature*, 341:544–546 (1989).

Hudson, P., et al., "DAbs and FAbs take on mAbs", *Today's Life Science*, 38 (1990).

Davis, G.T., et al., "Single Chain Antibody (SCA) Encoding Genes: One–Step Construction and Expression in Eukaryotic Cells", *Bio/Technology* 9:165–169 (1991).

Huston, J.S., et al., "Protein Engineering of Antibody Binding Sites: Recovery of Specific Activity in an Anti–Digoxin Single–Chain Fv Analogue Produced in *Escherichia col*" *Proc. Natl. Acad. Sci. USA*, 85:5879–5883 (1988).

Glockshuber, R., "A Comparison of Strategies To Stabilize Immunoglobulin $F_v$–Fragments", *Biochemistry*, 29:1362–1367 (1990).

Pack, P., et al., Miniantibodies: Use of Amphipathic Helices To Produce Functional, Flexibly Linked Dimeric $F_v$ Fragments with High Avidity in *Escherichia coli*, *Biochemistry*, 31(6):1579–1584 (1992).

Holliger, P., et al., "Diabodies: Small bivalent and bispecific antibody fragments", *Proc. Natl. Acad. Sci. USA*, 90:6444–6448 (1993).

Hamers–Casterman, C., "Naturally occurring antibodies devoid of light chains", *Nature*, 363:446–448 (1993).

Shitara, K., et al., "A new Vector for the High Level Expression of Chimeric Antibodies in Myeloma Cells", *Journal of Immunological Methods*, 167:271–178 (1994).

(List continued on next page.)

*Primary Examiner*—James C. Housel
*Assistant Examiner*—Bao-Thuy L. Nguyen
*Attorney, Agent, or Firm*—Walter H. Dreger

[57] ABSTRACT

An isolated immunoreactive molecule (IRM) capable of binding to a target molecule from at least one species or sub-species of the insect but not to at least one other species or sub-species of insect and a method of identifying one or more insect species or subspecies and kits therefor. The invention is particularly useful for distinguishing between Lepidopterans such as *Helicoverpa armigera* and *H. punctigera*.

18 Claims, 8 Drawing Sheets

OTHER PUBLICATIONS

Alting–Mees, M., et al., "Monoclonal Antibody Expression Libraries: A Rapid Alternative to Hybridomas", *Strategies in Molecular Biology,* 3(1):1–9 (1990).

Clackson, T., et al., "Making antibody fragments using phage display libraries", *Nature,* 352:624–628 (1991).

Engelhardt, et al., "Two–Step Cloning of Antibody Variable Domains in a Phage Display Vector", *BioTechniques,* 17(1):46 (1994).

Owens, R.J., et al., "The Genetic Engineering of Monoclonal Antibodies", *Journal of Immunological Methods,* 168:149–165 (1994).

Miura K et al. Identification and properties of lipophorin of the Silkworm, Bombyx mori. Comprehensive Biochemistry and Physiology 89 (B) (1) 95–103, 1988.

Ryan, R.O., et al. Chemical and Immunological Properties of Lipophorins from Seven Insect Orders. Archives of Insect Biochemistry & Physiology 1:375–383, 1984.

Kawooya, J.K. Role of Lipophorin in Lipid Transport to the Insect Egg. The Journal of Biological Chemistry 263:(18): 8748–8753, 1988.

Harlow, E. et al. Antibodies: A Laboratory Manual. Cold Spring Harbor, NY, Cold Spring Harbor Laboratories, 1988. pp. 288–318, 321–323, 334–351, 612.

Sevier E D et al. Monoclonal Antibodies in Clinical Immunology. Clin. Chem 27(11): 1797–1806, 1981.

Van der Horst, D.J., et al. Adipokinetic hormone–induced . . . Insect Biochemistry 17(6) 799–808, 1988.

Haunerland N H et al. Binding of insecticides to Lipophorin and Arylphorin, two Hemolymph proteins of *Heliothis zea*. Archives of Insect Biochemistry and Physiology 3: 87–96, 1986.

Miller SG et al. Binding of Riboflavin to lipophorin and a hexameric protein in the hemolymph of *Heliothis virescens*. Insect Biochemistry and Molecular Biology 22(6): 571–583, 1992.

Fitt, G.P. The Ecology of Heliothis species in relation to AgroEcoSystems. Annual Review of Entomology 34: 17–52, 1989.

Voller, A. et al "Enzyme immunoassays" Ch6 in *Alternative Immunoassays* ed W.P. Collins 1985 John Wiley & Sons Ltd. pp. 77–86.

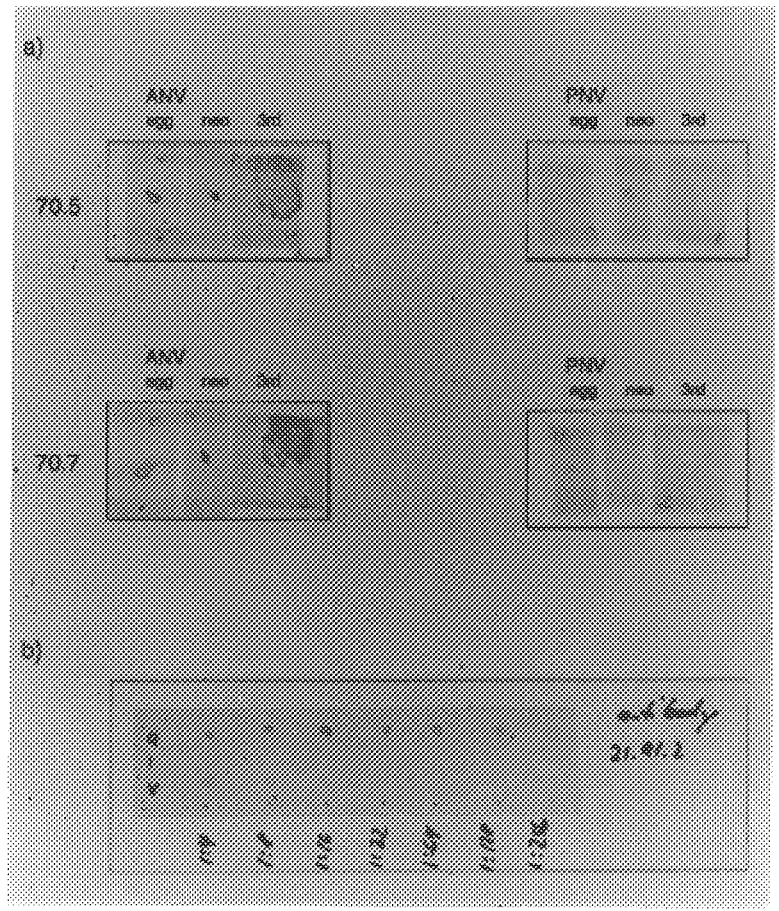
FIG._1

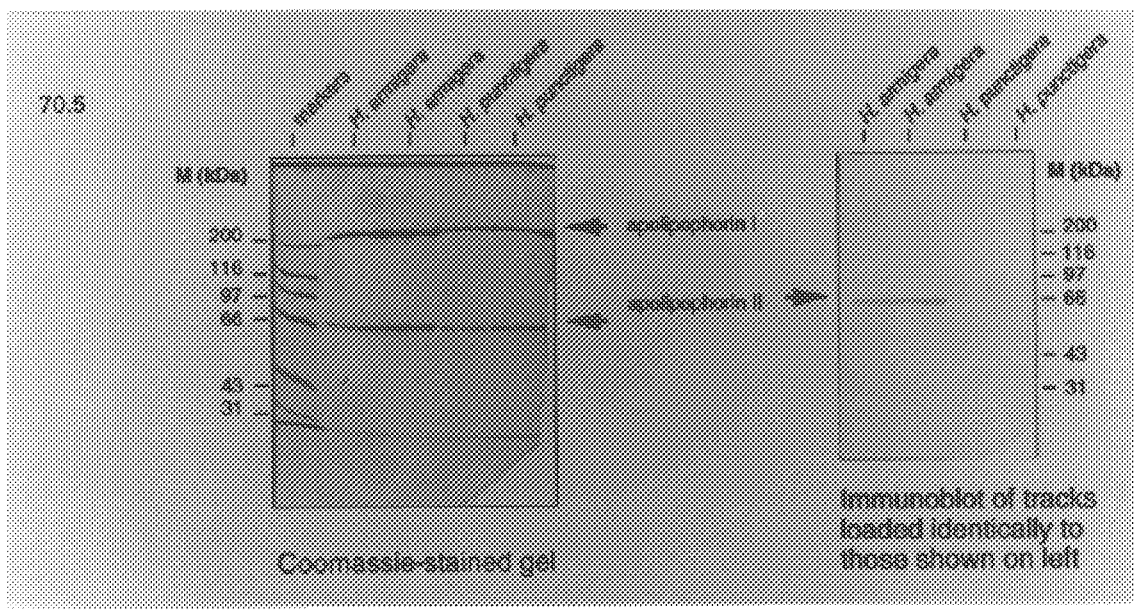
FIG._2

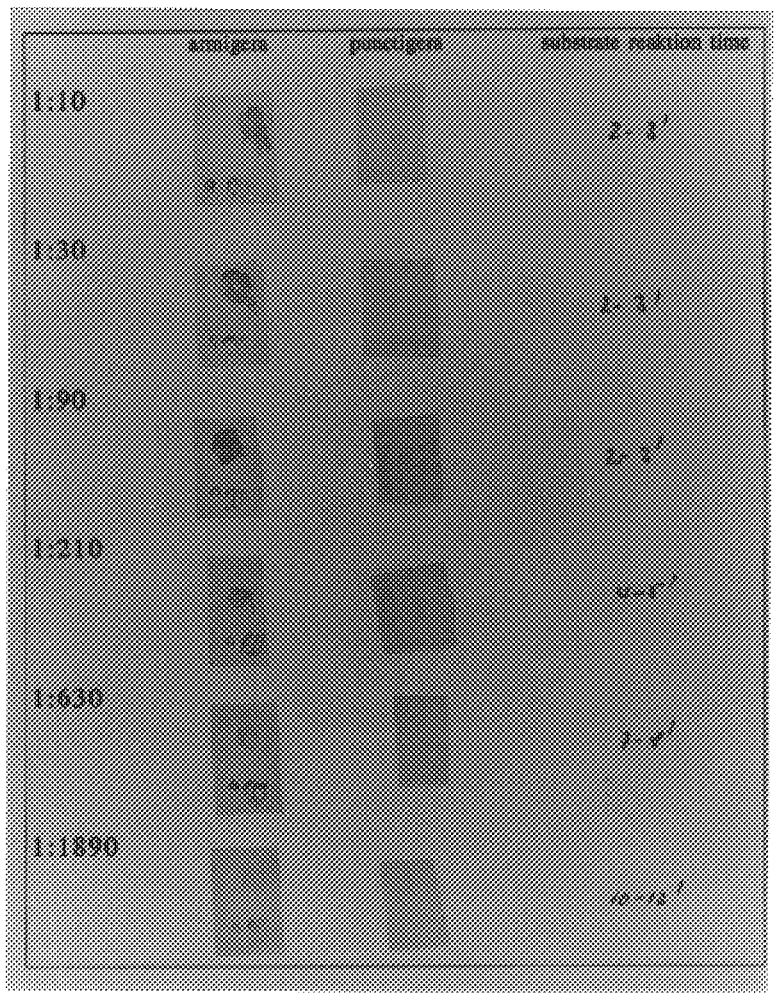
FIG._3

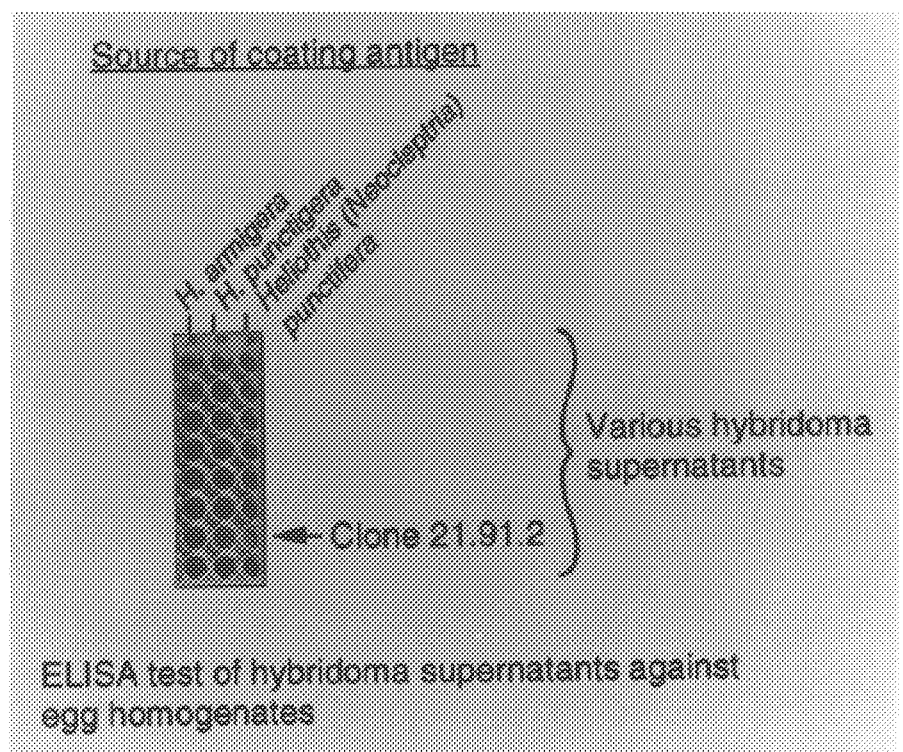
FIG._4

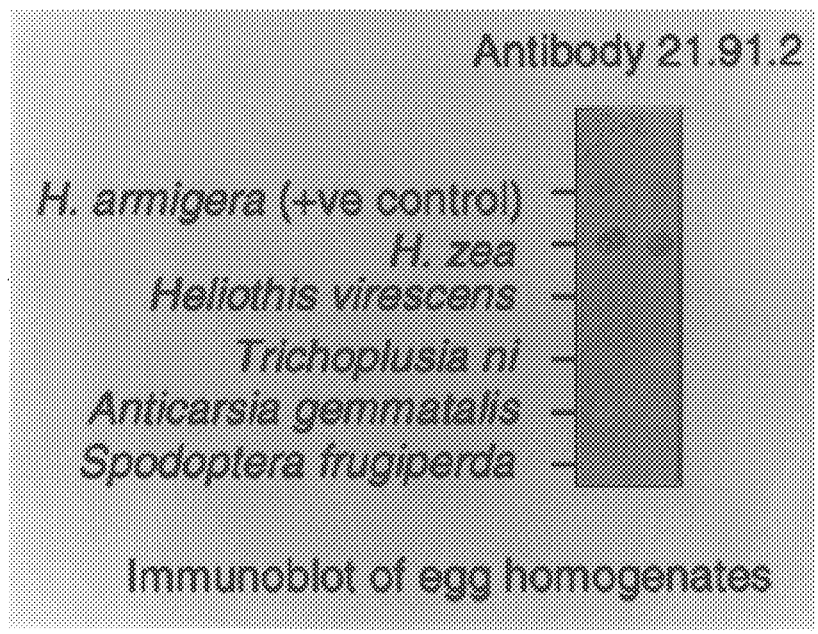
FIG._5

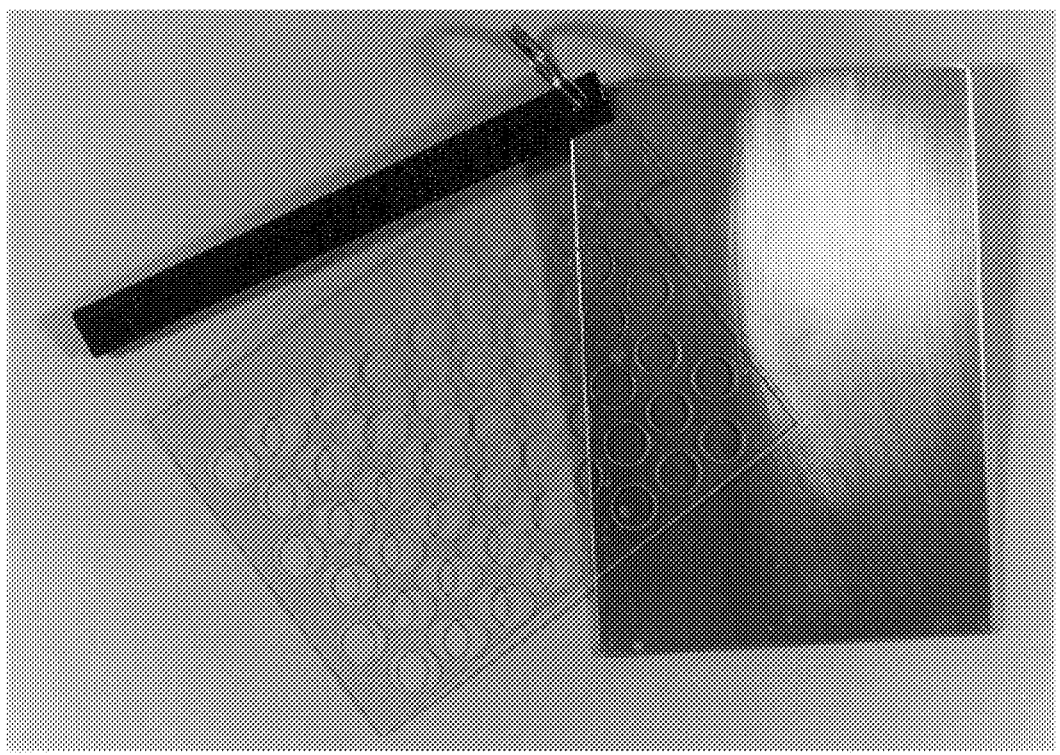
FIG._6a

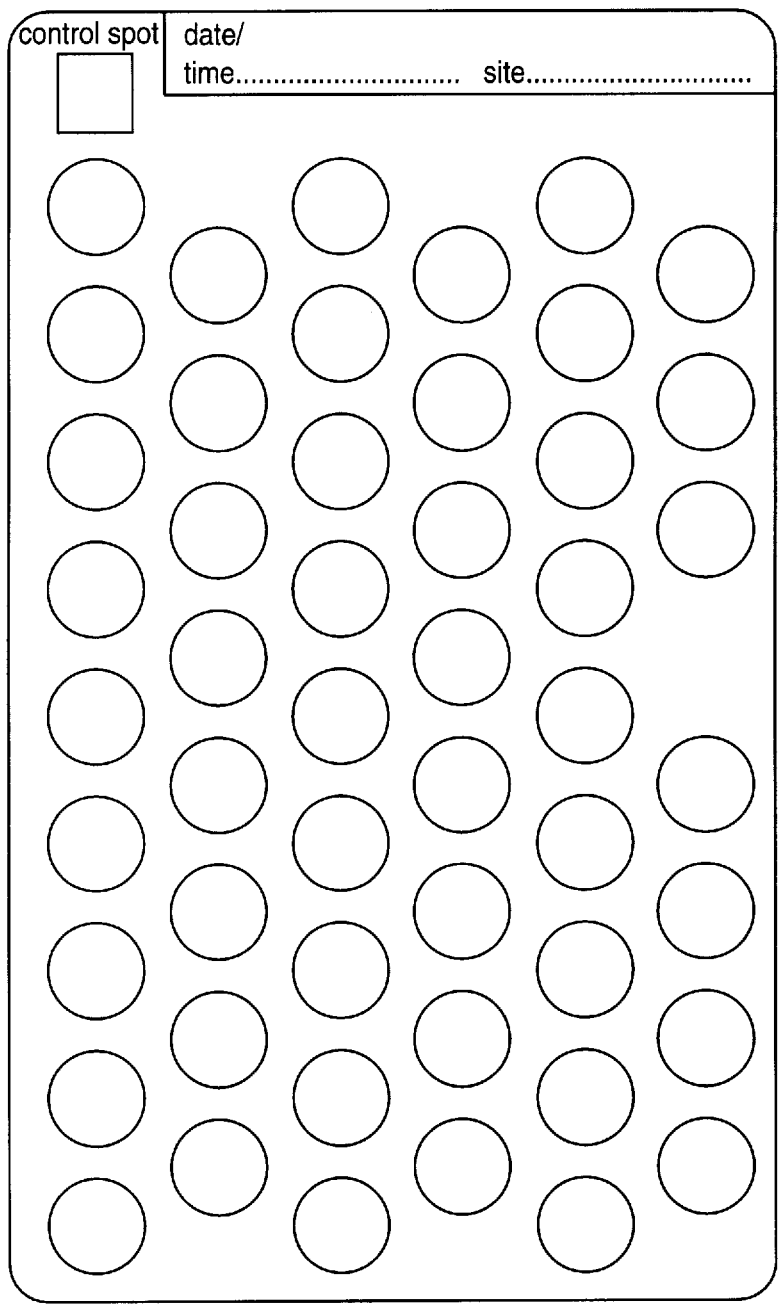
FIG._6b

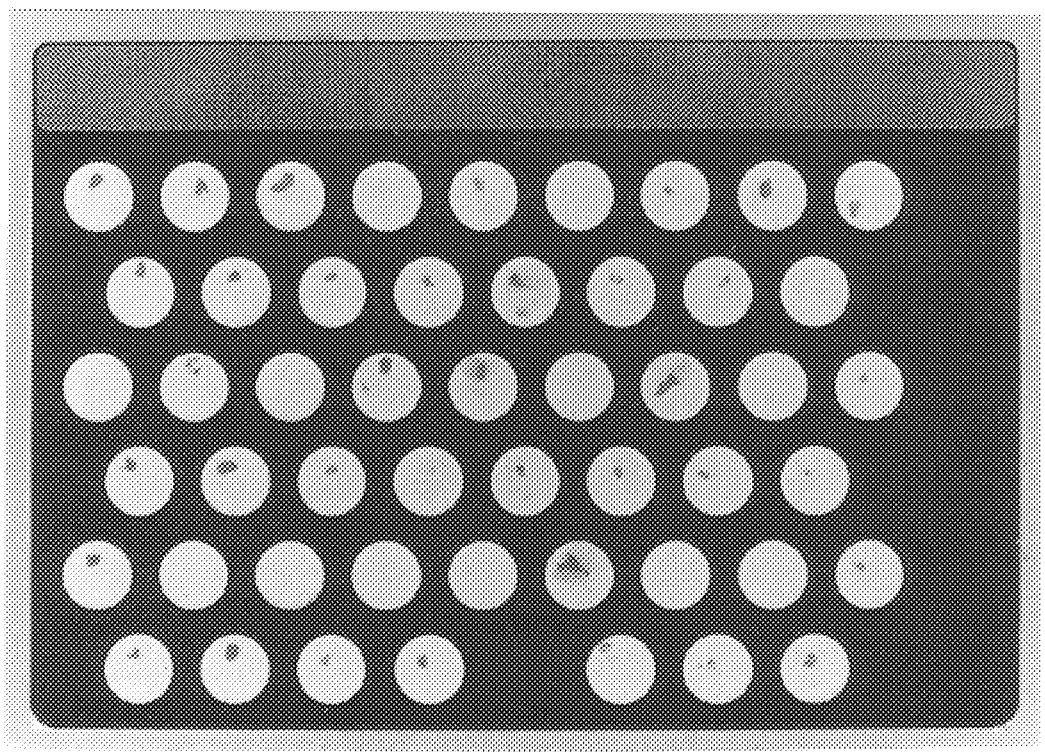
FIG._7

AGENTS AND METHOD FOR IDENTIFYING INSECTS

FIELD OF THE INVENTION

The present invention relates generally to an immunologically reactive molecule (IRM) capable of binding to a target molecule from at least one species of insect but not from at least one other species of insect. The present invention also contemplates a method of distinguishing between, or identifying, one or more insect species or subspecies.

BACKGROUND OF THE INVENTION

Insect damage to crops is a significant factor in decreasing crop yield and considerable effort is expended annually in controlling insect populations to minimise or prevent crop damage. Although chemical insecticides have played an important role in controlling insect populations, increasing resistance to these insecticides and environmental concerns have rendered the use of chemical insecticides less appealing.

Resistance Management Strategies (RMS's) have been developed in order to minimise insecticide resistance and usually involve the administration of more than one insecticide. However, such strategies are significantly more expensive, are time consuming and do not address the environmental concerns.

The insect genera Heliothis and Helicoverpa comprise economically important pests which attack a range of crops including cotton, tobacco, maize, sorghum, sunflower, soybean, chick peas and other pulses, rapeseed, canola, ground nuts, lucerne and many horticultural crops such as cut flowers and tomatoes and other vegetables (Fitt, 1989).

*Helicoverpa* (*Heliothis*) *armigera* and *Helicoverpa* (*Heliothis*) *punctigera* (Lepidoptera: Noctuidae) (hereinafter referred to as *H. armigera* and *H. punctigera*) cause crop damage which is economically significant to agricultural industry. Whilst *H. punctigera* is the more abundant species in Australia, *H. armigera* is considered the more problematic of the two because it has a history of developing resistance to the chemical insecticides which have been used in its control (Fitt, 1989). *Helicoverpa punctigera*, however, does not appear to have the same propensity for developing resistance to insecticides.

*Heliothis virescens* and *Helicoverpa zea* (hereinafter referred to as *H. zea*) are important pests of crops throughout North America and especially crops in the U.S.A. Whilst both species have developed resistance to some insecticides, (Fitt, 1989) they are distinguished by the fact that *Heliothis virescens* may display up to 150 fold resistance to synthetic pyrethroids whereas *H. zea* shows no detectable resistance to these compounds (Elzen et al., 1992). Synthetic pyrethroids are therefore more efficacious for control of *H. zea* than for *Heliothis virescens*.

*Heliothis virescens* is congeneric with *Heliothis* (*Neocleptria*) *punctifera* whereas *H. zea* is congeneric with *Heliocoverpa armigera* and *Helicoverpa punctigera*.

Resistance Management Strategies developed for *H. armigera* and *H. punctigera* have involved a rotation of pyrethroids, endosulfan and other insecticides to reduce exposure to endosulfan and pyrethroids. This has been necessary due to the increasing resistance to synthetic pyrethroids and endosulfan. Despite these RMS's, the frequency of resistant individuals has been steadily increasing (Forrester, 1990).

*Helicoverpa armigera* and *H. punctigera* at their egg and neonate stages are morphologically indistinguishable, whilst their respective larvae can only be distinguished by experts. A similar situation exists for *Heliothis virescens* and *H. zea*. Current RMS therefore make assumptions based on historical records of the relative abundance of the two species, averaged over wide geographical distances and several seasons. These assumptions necessarily entail some degree of inaccuracy, the consequence of which is that, in some cases, expensive alternative insecticides may be applied to *H. punctigera*, whilst in other cases, there may be multiple applications of pyrethroids to populations of *H. armigera*. In the latter case, the pyrethroid applications may be ineffective and will generally encourage the emergence of insecticide resistance. Similar problems also arise with *Heliothis virescens* and *H. zea*. Such situations may lead to unnecessarily expensive insect control for farmers. For example, insecticides such as pyrethroids which are adequate for species without a propensity to develop resistance are comparatively cheap insecticides. These may cost the farmer 3 or 4 times less to apply than those insecticides which are applied to insect species with a tendency to develop insecticide resistance. There is a need, therefore, to develop a convenient method to determine the species composition of egg lays, neonates or older larva which may have survived an insecticide application in the field. Such a method would be particularly useful for routine use by crop growers/farmers, agronomists and/or agricultural scientists so that insecticide applications can then be tailored to the composition of the Heliothis or Helicoverpa population actually present.

In work leading up to the present invention, the present inventors have found an immunologically reactive molecule (IRM) that distinguishes between insect species or subspecies. The IRM is capable of binding to a target molecule in at least one species or subspecies but does not react with at least one other species or subspecies. This provides a basis for distinguishing between or identifying insect species or subspecies.

SUMMARY OF THE INVENTION

Accordingly, one aspect of the invention relates to an immunologically reactive molecule (IRM) capable of binding to a target molecule from at least one species or subspecies of insect but not to at least one other species or subspecies of insect. The target molecule is an antigen which is present in insect tissues. These tissues may be those of eggs, neonates or older larvae.

Another aspect of the present invention contemplates a method of identifying one or more species or subspecies of insect by determining the reactivity of an IRM to a target molecule in a sample of insect material, wherein said IRM is capable of binding to the target molecule present in at least one of said species or subspecies but substantially not to any molecule of at least one other species or subspecies of insect. More particularly, the method comprises contacting a sample of insect material with an effective amount of an IRM specific for said target molecule of the one or more species or subspecies of insect for a time and under conditions sufficient for a complex to form between the target molecule and IRM, and then subjecting said complex to a detecting means.

Another aspect of the present invention relates to a kit for distinguishing between or identifying one or more insect species or subspecies from at least one other insect species or subspecies, said kit comprising in compartmentalised form a first compartment adapted to receive an IRM capable of binding to a target molecule of at least one species or subspecies of insect but not at least one other species or subspecies of insect and at least one other compartment adapted to contain a detector means.

In another aspect the instant invention relates to an isolated or purified preparation of a target molecule as herein described specific for a particular insect species or subspecies, to mutants and derivatives thereof and to the antigenic determinants of the target molecule.

In another aspect of the invention there is provided a method for making antibodies, particularly monoclonal antibodies, to said antigenic determinants for use in a method of detecting particular insect species. Antibodies can be made by standard techniques such as immunizing animals with insect extracts from said at least one species or subspecies and collecting the serum, identifying antibodies from said serum which are capable of binding at least one species or subspecies but not at least one other species or subspecies (Campbell (1984), Goding (1983) and Harlow and Lane (1988)).

DETAILED DESCRIPTION OF THE INVENTION

The present invention is predicated in part on the surprising discovery that different species or subspecies of insects that are morphologically indistinguishable for at least a part of their life cycles can be differentiated by an IRM which is capable of binding a target molecule present in one species or subspecies but is not capable of binding a molecule in one other species or subspecies.

Accordingly, one aspect of the invention relates to an IRM capable of binding to a target molecule from at least one species or subspecies of insect but not to at least one other species or subspecies of insect. The target molecule is an antigen which is present in insect tissues. These tissues may be those of eggs, neonates or older larvae. Preferably the target molecule is present in older larvae and neonates, more preferably the target molecule is present in eggs, still more preferably it is present in eggs and neonates. Even more preferably the target molecule is present in eggs, neonates and older larvae. Most preferably the target molecule is abundantly present in all life stages of the insect, including the egg, neonate and older larval stages. In one aspect of the invention the target molecule is lipophorin, a protein which is present in insects at all stages during their life cycles.

The term "subspecies" used herein refers to different strains, varieties, serotypes, subserotypes and/or other categories/groups/strains/varieties of insects within one species, genus or order. Although specific Lepidoptera are mentioned herein the invention covers Lepidoptera generally and other insect groups.

Preferably the IRM is in isolated form meaning it is in a state different to that found in nature. Advantageously, the isolated IRM is biologically pure meaning that a composition comprises, at least 20%, preferably at least 30% more preferably at least 40–50%, still more preferably at least 60–75%, and more preferably at least 85–95% of IRM as determined by weight, activity, immunological reactivity or other convenient means.

The IRM is preferably an antibody and advantageously a monoclonal antibody (mAb). The term "antibody" includes naturally occurring antibodies, recombinant antibodies, synthetic antibodies including fusions or chimers of antibodies and fragments of any of the foregoing such as Fab and F(ab')$_2$. Where the antibody IRM is a recombinant form, the molecule may be encoded by a naturally occurring or synthetic nucleotide sequence and expressed in any convenient expression system. Where the molecule is synthetic, it is conveniently prepared by the step-wise addition of single amino acid groups or amino acid fragments of, for example antibodies. With regard to the latter, the synthetic antibody may be a fusion or chimeric antibody comprising light or heavy chains derived from other antibodies.

Antibodies and other IRM's of the present invention may be of any animal origin including mammals such as humans, live stock animals, companion animals, wild animals and laboratory test animals (eg. mice, rats, rabbits and guinea pigs). An "animal" also extends to non-mammalian species such as birds (eg. chickens and other poultry, emus and ostriches).

The IRM may be labelled with a reporter providing, under suitable conditions, a detectable signal. Such reporters may include molecules such as radio-nucleotides, chemiluminescent molecules, bioluminescent molecules, fluorescent molecules or enzymes amongst others. Commonly used enzymes include horseradish peroxidase, glucose oxidase, β-galactosidase and alkaline phosphatase, amongst others. Alternatively the reporter may consist of particles including colloidal gold, latex microbeads or erythrocytes amongst others. In a further alternative the reporter may comprise a physical detector means such as biosensors, for example surface plasmon resonance.

Although not intending to limit the present invention to any one theory or proposed mode of action, the basis of the differential reactivity of the immunologically reactive molecules may be due to differences in antigenic determinants on the molecule for which they are specific. This could be due to changes or alterations in protein, carbohydrate or lipid molecules or combinations thereof, or to conformational changes, whether or not resulting therefrom. Thus in the case of lipophorin, in one embodiment of the invention, the IRM is reactive with the lipophorin of *H. armigera* but not the lipophorin of *H. punctigera*.

In a preferred aspect of the present invention the IRM is capable of binding a target molecule of at least one species or subspecies of Helicoverpa or Heliothis but not at least one other species or subspecies of Helicoverpa or Heliothis. Preferably the IRM is an antibody capable of binding to a target molecule of *H. armigera* not *H. punctigera*. Alternatively, preferably the IRM is capable of binding a target molecule of *H.zea* but not *Heliothis virescens*. Preferably, the target molecule for which the IRM is specific is an antigen present in egg or neonate tissues.

In its most preferred form, the present invention provides monoclonal antibodies mAb 70.5 and mAb 70.7 which bind *H. armigera* not *H. punctigera*. A hybridoma producing mAb 70.5 was deposited on Jan. 21st, 1993 at the European Collection of Animal Cell Cultures, Public Health Laboratory Service, Porton Down, Salisbury, U.K. and given accession number 93012101.

In another most preferred form, the present invention provides monoclonal antibody mAb 21.91.2 which binds *H. zea, H. armigera,* or *H. punctigera* and not to *Heliothis virescens* or *Heliothis (Neocleptria) punctifera.*

Another aspect of the present invention contemplates a method of identifying one or more species or subspecies of insect by determining the reactivity of an IRM to a target molecule which may be present in a sample of insect material, wherein said IRM is capable of binding to a target molecule present in at least one of said species or subspecies but substantially not to any molecule of at least one other species or subspecies. More particularly, the method comprises contacting a sample of insect material with an effective amount of an IRM specific to said target molecule of the one or more species or subspecies of insect for a time and under conditions sufficient for a complex to form between the target molecule and IRM, and then subjecting said complex to a detecting means.

The term "a sample of insect material" used herein means a sample of insect dervied from any life stage, or part of an insect, such as the eggs, larval or adult stages.

Preferably, IRM is an antibody as defined above, and is most preferably a mAb. Most preferably, the antibody is specific for a target molecule of *H. armigera* not *H. punctigera*. Alternatively most preferably the antibody is specific for a target molecule of *H. zea* not *Heliothis virescens*. Still more preferably the antibody is specific for an antigen present in egg or neonate tissues. Most preferably the IRM is specific for lipophorin of *H. armigera* not *H. punctigera*. Suitable antibodies include mAb 70.5 and 70.7. Alternatively the IRM is specific for a target molecule present in *H. zea* not *H. virescens*. Suitable antibodies include mAb 21.91.2.

Detection of binding of the IRM to the target molecule can be determined by any convenient means. Preferably, the target molecule is detected by an IRM which is labelled directly by a reporter as herein described, such as by a reporter enzyme, or by reporter particles such as colloidal gold or by physical means such as biosensors. Alternatively, the presence of antigen-antibody complex may be detected by an anti-immunoglobulin labelled with a label, reporter or other detector molecule capable of providing a detectable signal. In this embodiment, the anti-immunoglobulin binds to the bound target molecule reactive antibody and then the label, reporter or detector molecule is read. Suitable reporters are as hereinbefore described.

The target molecule containing sample is preferably in the form of eggs or larvae but may be from later life stages of the insect. The sample may be contacted with, preferably squashed onto any conventional material such as a polymer or glass, the most commonly used polymers being cellulose (including paper) nitrocellulose, polyacrylamide, nylon, polystyrene, polyvinylchloride, polyvinylidene difluoride (PVDF) or polypropylene.

The immunologically reactive molecule of the present invention may also be bound to a solid support such as those listed above.

Another aspect of the present invention relates to a kit for distinguishing between, or identifying, one or more insect species or subspecies from at least one other insect species or subspecies, said kit comprising in compartmentalised form a first compartment adapted to receive an IRM capable of binding to a target molecule of at least one species or subspecies of insect but substantially not at least one other species or subspecies of insect, and at least one other compartment adapted to contain a detector means. In a preferred form, the IRM is bound to a support as herein before described, more preferably a solid support. Most preferably the solid support comprises sheet material such as a membrane.

Preferably the kit comprises an IRM reactive with *H. armigera* not *H. punctigera*. Most preferably the kit comprises mAb 70.5 or mAb 70.7.

The detection means preferably comprises a reporter or label as described herein which can detect the binding of the IRM to the target molecule.

In one preferred aspect, the kit comprises a mAb specific for the target molecule directly conjugated with a detectable reporter such as an enzyme, and where appropriate enzyme substrate and suitable buffers. In a more preferred aspect the kit comprises mAb 70.5 or 70.7 conjugated with horseradish peroxidase, alkaline phosphatase or β-galactosidase, enzyme substrate and appropriate buffers.

In another preferred aspect the kit comprises an anti-immunoglobulin which binds the antibody-target molecule complex. The anti-immunoglobulin is labelled with a label, reporter or other detector as herein described capable of providing a detectable signal.

In another aspect the instant invention relates to an isolated or purified preparation of a target molecule as herein described specific for a particular insect species or subspecies, to mutants and derivatives thereof and to the antigenic determinants of the target molecule. The antigenic determinants of the instant invention may comprise the amino acid/polypeptide, lipid and/or polysaccharide portion of the target molecule. Such mutants and derivatives of the target molecule or the antigenic determinants thereof may be produced by natural chemical and/or recombinant means.

The term "mutant" used herein refers to a variant of apolipophorin which while different from native apolipophorin retains substantially the same biological or immunological characteristics of apolipophorin. The term "derivative" used herein refers to a molecule derived from apolipophorin which while different from native apolipophorin retains substantially the same biological or immunological characteristics as apolipophorin.

In a most preferred embodiment the invention relates to a purified preparation of lipophorin, the 70 kDa apolipophorin II and 230 kDa apolipophorin I subunits of lipophorin from *H. armigera, H. punctigera, H. zea* or *Heliothis virescens* and to mutants and derivatives thereof.

In another aspect of the invention there is provided a method for making antibodies, particularly monoclonal antibodies, to said antigenic determinants for use in a method of detecting particular insect species. Antibodies can be made by standard techniques such as immunizing animals with insect extracts from said at least one species or subspecies and collecting the serum, identifying antibodies from said serum which are capable of binding at least one species or subspecies but not at least one other species or subspecies (Campbell (1984), Goding (1983) and Harlow and Lane (1988)). Alternatively the antibodies can be made by isolating immune cells from animals which have been immunised with insect extracts and fusing the immune cells with immortalising cells to produce immortalised cells and identifying antibodies from the immortalised cells which are capable of binding to a molecule from at least one species or subspecies of insect but not to at least one other species or subspecies of insect. Similarly monoclonal antibodies can be made by in vitro immunisation which involves taking immune cells from an animal, which animal may or may have been immunised with an insect extract, exposing the cells so removed to the insect extract and fusing the cells with an immortalising cell line as described above. The immortalising cells may be screened in the manner described above. As stated above mAbs can be made according to standard techniques including that described below.

The present invention is further described by reference to the following non-limiting figures at Example.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1: is a photographic representation of an immunoblot testing specificity of mAbs for *H. armigera*.

FIG. 2: is a photographic representation of an immunoblot testing specificity of mAb 70.5 against subunits of *H. armigera* and *H. punctigera* lipophorin.

FIG. 3: depicts titrations of mAb-HRP conjugate.

FIG. 4: depicts ELISA tests of mAb 21.91.2 with egg homogenates.

FIG. 5: is a photographic representation of an immunoblot testing mAb 21.91.2.

FIG. 6a): is a diagrammatic representation of a kit solid support holder.

FIG. 6b): depicts a membrane printed with guide markings.

FIG. 7: Test results (where the red material indicates *H. armigera*).

EXAMPLE 1

1. Materials & Methods

Helicoverpa culture

The AN strain of *H. armigera* and the PUNC strain of *H. punctigera* were used for all immunisations and preliminary screening. Colonies were cultured in the laboratory on artificial diet (Teakle, 1985).

Antigen preparation

Whole eggs or larvae of each species were snap frozen and stored at −80° C. Tissue was thawed into 10–20 volumes of ice-cold phosphate buffered saline containing 5 mM PMSF, 5 mM EDTA, 0.1 $\mu gmL^{-1}$ pepstatin and a few crystals of phenylthiourea, and disrupted with a motor-driven teflon in glass homogeniser. The homogenate was filtered through glass wool and then centrifuged at 240,000 g for 45 min. The supernatant was concentrated to 3 $mgml^{-1}$ in normal saline using a centricon 10 (Amicon) concentrator and the pellet was resuspended in 1 mL saline. Both were frozen prior to use for immunisation or screening.

Haemolymph was collected from fifth instar larvae by snipping off a proleg and collecting the exudate into an equal volume of ice-cold phosphate buffered saline containing 10 mM PMSF, 10 mM EDTA, 0.2 $\mu gmL^{-1}$ pepstatin 20 $\mu M$ E64, 10 mM 1,10 phenanthroline, 20 mM thioglycerol and a few crystals of phenylthiourea.

To fractionate Helicoverpa proteins, whole eggs were homogenised, separated in a discontinuous SDS-PAGE system (Laemmli, 1970) and electroblotted to a nitrocellulose membrane. The membrane was stained with Coomassie Blue R-250. Major proteins and intervening regions were excised, ground up and stored for use an immunogen.

To obtain pure proteins for immunisation, haemolymph from 5th instar larvae was separated by native PAGE, blotted to nitrocellulose and bands which were unique to one or other species were prepared for use as antigen, as described above.

Immunisation

Primary immunisations were performed s.c. and comprised a 1:2 mixture of antigen in saline with Freund's complete adjuvant. Subsequent immunisations were generally performed i.p. at 4 week intervals with a 1:2 mixture of antigen with Freund's incomplete adjuvant. After 4 immunisations, mice were rested until serum titre was close to control values. Selected mice were given intra-peritoneal booster injections with antigen in saline on the four successive days prior to performing the fusion.

Fusions

Fusions of immune spleen cells to $SP_2O$ or Ag8 cells were performed according to standard procedures (Harlow and Lane 1988) and hybridomas were selected with hypoxanthine (13.6 $\mu gmL^{-1}$) and azaserine (1 $\mu gmL^{-1}$). Hybridomas were initially grown in medium supplemented with 20% foetal bovine serum (FBS)+2% horse serum which was reduced to 10% FBS when cells were growing strongly in a 24 well plate. Fusions were routinely plated into 10–20 96 well plates.

Screening

As soon as colonies were visible macroscopically, supernatants were screened by indirect ELISA using Nunc Immunoplate II microplates. For preliminary screens, plates were coated with a mixture of total *H. armigera* and *H. punctigera* homogenate at a ratio of 62.5 $\mu g$ of eggs/well, equivalent to approximately 1 egg per well. Positives were detected using a two step, second antibody-biotin, streptavidin-horseradish peroxidase (Amersham), system.

To identify differential responders, positive clones were re-screened separately against *H. armigera* and *H.punctigera*.

Isotyping of monoclonals was performed using Amersham's mouse monoclonal isotyping kit.

Medium-scale production and purification of antibodies

Clones 70.5 and 70.7 were grown in 175 $cm^2$ flasks using standard RPMI medium with 1% (v/v) foetal bovine serum, Nutridoma SR (Boehringer-Mannheim) or Monomed A (CSL). The combined supernatants (approximately 4.5 liters of 70.5 and 4 l of 70.7) were harvested by centrifugation and concentrated 10 to 20 fold over a Millipore PTTK membrane with nominal 30 kDa cut off. Antibodies were precipitated with 50% (w/v) ammonium sulphate, resuspended in 20 mM sodium phosphate buffer, pH 7 and dialysed extensively against the same buffer. The sample was filtered and loaded onto a 5 mL protein G column (Hitrap, Pharmacia), which was washed with 20 mM sodium phosphate buffer and eluted with 0.1 M glycine-HCl pH 2.7. Antibody containing fractions were adjusted to pH 7–7.5 by the addition of 0.1M TrisHCl pH 9.0.

Antibody conjugation

Antibody conjugation was performed using the periodate coupling method, essentially according to Polak and Kristek (1988). However, dialysis, rather than gel filtration, was used to remove low molecular weight contaminants, following the conjugation reaction. Conjugated antibody was used without further purification.

Concentrations of purified antibody were estimated by $Abs_{280nm}$ using the relationship:

$$[Ig] = \frac{Abs_{280nm}}{1.4}$$

Conjugate concentrations were estimated on the assumption that $[conjugate](mg/mL) = Abs_{280nm}$.

2. Results

Immunologically Reactive Molecules

Generation of monoclonal antibodies

A total of 135 mice were immunised with Helicoverpa proteins. Seventy one mice received crude antigens prepared from a single species. Twenty two mice were immunised with broad molecular weight cuts of the proteins from a single species separated by SDS-PAGE and 6 mice were immunised with individual, species-specific, bands purified from haemolymph using non-denaturing PAGE. Thirty six mice were immunised with antigens from one species, followed by a treatment with cyclophosphamide and then antigens from the second species. Further details of antigen sources are provided in Table I.

Thirty-four mice were selected for fusions. Fusions performed from mice with high serum titre typically yielded one or more growing colonies in 30–100% of wells. All discriminating antibodies were obtained from fusions relying on immunisations of crude soluble antigen. The serum titre of mice receiving purified antigens remained low after four immunisations and fusions performed with them yielded few positive secretors and no discriminating antibodies. The aim of the cyclophosphamide treatment is to eliminate the immune response to antigens that are common to both species (Matthew and Patterson 1983; Lewis et al 1987). The mice were immunised with a highly diverse mixture of antigens. It was found that a single cycle of immunisation followed by cyclophosphamide treatment (40 mg/kg, i.v. or i.p. on three successive days) did not significantly depress the serum titre measured after a second immunisation. In order to remove the immune response to the first species it was necessary to repeat the cyclophosphamide treatment after a second boost with antigen. This treatment succeeded in suppressing the immune response to the first species but no significant difference in the response could be elicited following subsequent immunisations with antigens of the second species. Fusions performed with spleens from these mice yielded few colonies and no differential responders.

Three primary clones which strongly discriminated amongst Australian heliothines were subcloned and stable subclones were selected for further investigation. Subclones 70.5.31.11 and 70.7.88.1 recognised *H. armigera* but displayed no significant reaction against *H. punctigera* (FIG. 1). For brevity these two subclones are referred to below as 70.5 and 70.7. Subclone 21.91.2 recognised *H. armigera, H. punctigera* and *H. zea* but did not recognise *Heliothis (Neocleptria) punctifera*, or *Heliothis virescens*.

Characterisation of monoclonals

Isotype

MAbs 70.5 and 70.7 were both of the IgG$_1$ subclass with κ-light chains.

Species- and stage-specificity

Preliminary ELISA tests showed that mAbs 70.5 and 70.7 reacted against an egg homogenate of *H. armigera* but not *H. punctigera*. As shown in FIG. 1, the discrimination between *H. armigera* and *H. punctigera* was also observed in a squash immunoblot format and extended to all life-stages (older larvae, pupae and adults not shown).

Strain-specificity

A number of distinct strains of *H. armigera* and *H. punctigera* were tested in order to determine whether the specificity reflected an antigen diagnostic for the two species or was limited to a particular population of either species. As shown in Table II, *H. armigera* from all sources, including morphologically defined *H.armigera* specimens from India and China gave a positive signal, whilst *H. punctigera* never reacted positively.

Identity and distribution of antigen

An immunoaffinity column was prepared by coupling approximately 5 mg of purified mAb 70.7 to 1 mL of cyanogen-bromide activated Sepharose according to the manufacturers instructions. The Sepharose column was used to perform an immunoaffinity purification from diluted 5th instar *H. armigera* haemolymph. SDS-PAGE analysis revealed that two polypeptide bands with Mr of ≅70,000 and ≅200,000 were specifically enriched from whole haemolymph. However an immunoblot of a parallel gel revealed that only the 70 kDa protein was recognised by the monoclonal.

It was concluded that mAb 70.7 recognised the small subunit of a relatively abundant haemolymph protein comprising two polypeptide subunits of ≅70 and ≅230 kDa. Other data, showed that mAb 70.5 also reacted specifically against 70 kDa protein present in haemolymph and eggs. Subunit molecular weights of 230–250 kDa and 70–85 kDa are characteristic of the lipophorin class of insect proteins (Beenakkers et al 1988). These data are therefore consistent with both monoclonals recognising apolipophorin II a subunit of "lipophorin" the major insect lipid transport and storage protein.

In order to test this hypothesis lipophorin was purified from the haemolymph of 5th instars of both species using flotation on a KBr density gradient. The buoyant densities of the lipophorins from both species were approximately 1.17 to 1.18 g/ml as determined by refractometry. This is consistent with their classification as high density lipophorins (HDLp) (Beenakkers et al 1988). As shown in FIG. 2, mAbs 70.5 and 70.7 both recognised the 70 kDa subunit of *H. armigera* lipophorin but there was no reaction against the purified protein from *H. punctigera*.

An immunofluorescence survey of whole teased neonate larvae was performed and analysed using the laser confocal microscope. Diffuse staining was observed throughout the abdomen with concentrations of fluorescence in the posterior of the abdomen and in the thorax. The former staining appeared to be coating the convolutions of the malpighian tubules whilst the thoracic immunofluorescence was associated with an unidentified folded or involuted structure. No intracellular staining was observed.

Lipophorin is known to be synthesised in the larval fat body of Lepidoptera and exported into the haemolymph. Lipophorin is also laid down in the eggs of lepidopterans during vitellogenesis. These tissues were examined for immunoreactivity by SDS-PAGE and immunoblotting using mAb 70.5. Control tissues, body wall, including muscle and epidermis, and *H. punctigera* eggs showed no immunoreactivity. The 70 kDa band was prominent in the lanes containing *H. armigera* haemolymph and eggs. In the haemolymph lane there was evidence of some partial proteolysis giving rise to a minor immunoreactive band of lower molecular weight. The particulate fraction of fat body showed a prominent immunoreactive band at approximately 120 kDa but there was no immunoreactivity at 70 kDa nor indeed in the soluble fraction of that tissue. These data, are consistent with the known distribution and biochemistry of lipophorin.

Quantity of lipophorin in Helicoverpa eggs and haemolymph

Eggs of *H. armigera* and *H. punctigera* both contained 68 mg soluble protein/g of eggs as measured by a modification of the Lowry assay (Lowry et al., 1951; Markwell et al., 1978; Wessel & Flügge 1984). There were no previous estimates of the composition of eggs of *H. armigera* or *H. punctigera,* however data obtained in the sphingid *M. sexta* indicates that lipophorin represents approximately 4.2% of soluble egg protein, and 1.3% of total egg weight (Kawooya and Law, 1988). For a Helicoverpa egg with a mean weight of 62.5 μg this would predict 0.2–0.8 μg of lipophorin per egg.

Similarly, most studies of lepidopteran haemolymph deal with pupal or adult haemolymph and there is no published data dealing specifically with the concentration of lipophorin in the larval haemolymph of any heliothine moth. We estimated the protein concentration of fifth instar *H. armigera* haemolymph as 6.55±1.5 mg/mL. We can obtain some indication of the likely concentration of lipophorin from early work on the lipoproteins found in pupal haemolymph of *Hyalophora cecropia* (Thomas and Gilbert, 1968) which indicates that concentration of lipophorin is approximately 1.2 mgmL$^{-1}$. This would represent approximately 5–10% of total haemolymph protein, which is generally compatible with values reported for larval or nymphal forms in other orders (Engelmann et al., 1988).

Construction and testing of a direct conjugate

Fifty-six milligrams of mAb 70.5 and 43 mg of mAb 70.7 were purified from 4.5 liters and 4 liters of their respective culture supernatants. Similar amounts of mAb 70.5 have been purified from murine ascites fluid (approximately 2 mg/ml) and this mAb has also been conjugated as described below.

In order to develop a test for field use a direct conjugate of HRP to each of the monoclonals was produced. Equal weights of HRP (Cat. no. 814, Boehringer Mannheim) and antibody, i.e. an approximate ratio of 4 moles HRP per mole antibody, were coupled by the method of (Polak and Kristek 1988). Analysis of conjugation mixtures that had been purified over Sephacryl S300 indicated that over 65% of the haem groups were incorporated into material having an HRP to antibody coupling ratio of between 3.5 and 5.5.

Thirty-three mg of a conjugate of 70.5 and 60 mg of a conjugate of 70.7 were combined to give a total of 55.5 mL of a homogeneous batch suitable for laboratory and wide-scale field testing. The concentration of the conjugate was estimated at 1.68 mgml$^{-1}$. It was stored at 4° C. in Tris buffered saline at pH 7.5 with 2% BSA and 0.02% thimerosal added to enhance stability.

Titrations of the antibody (FIG. 3) indicated that good performance was achieved using an overall working dilution of 1/200 to 1/400 (i.e. approx. 4.2 µgml$^{-1}$). This was however modified to a working dilution of 1/40 (approx. 42 µg/mL) to increase the speed of the reaction without loss of specificity. In this case conjugate was diluted in 1% (w/v) teleostan gelatine, 2M NaCl, 20 mM TrisHCl pH 7.4, 0.01% (w/v) thimersal.

Field test kit

One test is based on a membrane squash principle. Statistical considerations indicated that 50 samples per test would offer a reasonably certain estimate of the percentage *H. armigera* whilst being practical to collect and test, however kits which accommodate up to 100 samples at a time can be used. The test kit comprises a reusable membrane holder, the membrane itself (optionally with printing thereon) and the solutions used to develop an *H. armigera*-specific reaction.

The membrane holder is constructed with an aluminium base-plate 16.5 cm×11.5 cm×2.5 mm. A polycarbonate sheet, 1 mm thick perforated by fifty 12.5 mm diameter holes, is placed over the base plate. The polycarbonate sheet is held in place by a length of plastic book spine, of the sort available from stationers, and a ring clip, which allows easy pivoting of the assembly. The membrane holder is shown in FIG. 6.

To use the kit, a supported nitrocellulose membrane (Amersham Hybond-C Super) is cut to 16.5 cm×10.5 cm and fitted between the base-plate and the perspex template. Alternatively a Sartorius membrane may be used since this appears to have good handling properties. Optionally a membrane with printed guide markings (as shown in FIG. 6b)) can be fitted instead. The membrane is secured in the cassette by a small bulldog clip. A positive control is provided in the upper right hand corner of the membrane. This comprises a 1 µl spot of a preparation of *H. armigera* haemolymph diluted to give a signal of comparable strength to a single egg of *H. armigera* collected in the field. The overall dilution factors used were in the range 1/60 to 1/120. In order to prevent contamination with leaf and larval peroxidases, membranes are pretreated for one hour in 5% BSA, followed by one hour in 5% BSA plus 5% diploma skimmed milk. Membranes were rinsed in 0.02% (w/v) thimerosal, dried and stored with desiccant at 4° C. prior to use.

In one embodiment of the kit, block solution was provided as 25 mL of 5% (w/v) teleostan gelatin in 2M NaCl, 0.01% (w/v) thimersal per membrane. Antibody was provided as 25 mL of mAb-HRP concentrate per four membranes. Wash solution was provided as 50 mL per membrane of a concentrate (5M NaCl, 100 mM Tris HCl pH 7.4, 0.5% (w/v) Tween 20, 0.01% (w/v) thimersal) which was diluted to 250 mL with tap water to use. Substrate was provided as two solutions, 20 mL per membrane of 0.0125% (w/v) urea hydrogen peroxide in 20 mM Tris HCl pH 7.4 and 10 drops (200 µl) per membrane of 30 mg/mL of 4-chloronaphthol in absolute ethanol, which were mixed on the membrane immediately prior to use. In this instance a published version of a single component HRP substrate was found to be unstable, (Brand 1990), furthermore it was found that the red precipitate produced by 3-AEC provided a distinct contrast with chlorophyll stains and is preferable to tetramethylbenzidine for this reason. It was subsequently found that 4-chloronaphthol in a pH 7.0–7.5 buffer gave lower background interference during colour development, and being purple was also clearly distinguishable from chlorophyll staining.

Kit use

Eggs and small larvae are squashed directly onto the membrane using the leaves that bear them until each of the 50 holes contain a squashed individual. After squashing the samples, the membrane was removed from the holder and stored, dry, until development. It was found that antigen could be detected immediately after squashing and remained recognisable after overnight incubation of the membrane at 60° C. or after incubation for six weeks at 37° C. Longer storage times were not tested. If the membrane was stored wet the potential to detect the antigen was rapidly lost even at 0° to 4° C.

One development procedure involves blocking the membrane for 1 minute, incubating the conjugate with the membrane for 5 minutes, three rinses with wash buffer over a period of 2 minutes, followed by incubation with substrate/colour developer for 30–60 seconds and a rinse in tap water to stop the reaction. Table III lists the steps involved in performing the test and FIG. 7 shows the results of a test performed under laboratory conditions.

EXAMPLE 2

1. Materials and Methods

Monoclonal antibody 21.91.2 was raised as described above. Australian Heliothinae were reared in the laboratory using standard procedures as described above.

American Lepidoptera were provided as frozen eggs by Dr. Matthew Greenstone USDA.

Species-specificity was determined using ELISA tests and immunoblots. Antigens were prepared so as to apply one egg equivalent per test well or test spot.

Preparation of antigen

For ELISA screening, approximately 6.25 mg of snap frozen eggs were thawed into each mL of coating buffer (0.1M sodium carbonate/bicarbonate pH 9.6) containing 0.5% (w/v) Tween 20 and homogenised using teflon in glass or glass on glass tissue grinders. The homogenates were clarified by centrifugation for 3 minutes at 14,000 g and 4° C. and diluted 10 fold in coating buffer without Tween 20.

Wells were coated with 100 μL of the clarified homogenate at 4° C. overnight.

For dot blot screening, snap frozen eggs were thawed into homogenisation buffer (ice-cold phosphate buffered saline containing 5 mM PMSF, 5 mM EDTA, 0.1 μgmL$^{-1}$ pepstatin and a few crystals of phenylthiourea) at a ratio of 62.5 mg per mL and homogenised using teflon in glass or glass on glass grinders. The homogenate was centrifuged for 3 minutes at 14,000 g and 4° C. and 1 μL aliquots were spotted directly onto the membrane and allowed to dry.

ELISA for testing discrimination of Australian heliothinae

Supernatants were screened by indirect ELISA using Nunc Immunoplate II microplates. Plates were coated with total egg protein homogenates from the following species: *Helicoverpa armigera* or *Helicoverpa punctigera* or *Heliothis* (*Neocleptria*) *punctifera* at a ratio of 62.5 μg of eggs/well, equivalent to 1 egg per well (Personal communication J. Fisk). The wells were blocked with a 1% (w/v) solution of skimmed milk powder and incubated with the mAb 21.91.2 supernatant. Positives were detected using a two step, second antibody-biotin, streptavidin-horseradish peroxidase, system (Amersham).

Immunoblots for testing discrimination of American Lepidoptera and titrating antigen 1 μL aliquots of egg homogenate, equivalent to 1 egg, were spotted onto Hybond C Super or Hybond C Extra strengthened nitrocellulose (Amersham) and allowed to dry. To titrate egg antigens versus mAb 21.91.2, a series of doubling dilutions of the egg homogenates were performed in homogenisation buffer. One μl aliquots of the diluted homogenates were spotted onto the nitrocellulose membrane and allowed to dry, so as to give spots equivalent to ¼, ⅛, ¹⁄₁₆ etc. of an egg. The membrane was blocked with a 5% (w/v) solution of skimmed milk powder and incubated with the mAb supernatants. Positives were detected using a two step, second antibody-biotin, streptavidin-horseradish peroxidase, system (Amersham).

2. Results and Discussion

MAb 21.91.2 was shown to recognise an egg antigen of *Helicoverpa armigera* and *Helicoverpa punctigera* but not of *Heliothis* (*Neocleptria*) *punctifera* (FIG. 4). On the basis of this discrimination, mAb 21.91.2 was selected for testing on American Lepidoptera (FIG. 5). The antibody recognised the positive control, *H. armigera* and also *H. zea* but not *Heliothis virescens*, *Trichoplusia ni*, *Anticarsia gemmatalis* nor *Spodoptera frugiperda*.

A second batch of supernatant from 21.91.2 was tested and, in this experiment, the immunoreactivity appears to be dependent on the concentration of egg proteins (FIG. 1b). The best discrimination was observed with dilutions of *H. armigera* and *Heliothis virescens* egg proteins of 1/32 or 1/64.

TABLE I

Sources of antigens used for immunisation program. Table indicates number of mice immunised for each source

|  | Eggs | | Larvae | | Adult | | |
| --- | --- | --- | --- | --- | --- | --- | --- |
|  | Sol | Part | Sol | Part | Sol | Part | Totals |
| Crude antigens: | | | | | | | |
| −cyclophosphamide | 18* | 4 | 25 | 18 | 4 | 2 | 71 |
| +cyclophosphamide | 13 | — | 7 | 10 | 4 | 2 | 36 |
| Size-fractionated antigen from whole eggs | 22 | | | | | | 22 |

TABLE I-continued

Sources of antigens used for immunisation program. Table indicates number of mice immunised for each source

|  | Eggs | | Larvae | | Adult | | |
| --- | --- | --- | --- | --- | --- | --- | --- |
|  | Sol | Part | Sol | Part | Sol | Part | Totals |
| Individual haemolymph bands from 5th instar larvae | | | 6 | | | | 6 |
| | | | | | | | 135 |

Approximately equal numbers of mice received antigens from each *Helicoverpa* sp. Fusions were performed using spleens from 34 of the best responding mice

TABLE II

Specificity of mAbs tested on individuals from various strains and field locations
Recognition of individual eggs and neonates by mAbs using an immunoblot

|  |  | mAb 70.5.33.11 | | mAb 70.7.88.1 | |
| --- | --- | --- | --- | --- | --- |
| Species/Strain | Origin | Eggs | Larvae | Eggs | Larvae |
| *H. armigera* | | | | | |
| AN | LAb Strain | + | + | + | + |
| ANV | Namoi Valley | + | n.d. | + | + |
| AMFO | Namoi Valley | + | n.d. | + | + |
| SUPER | Emerald | + | + | + | + |
| Field-caught | Namoi/Gwdir | + | + | n.d. | n.d. |
| Field-caught | ICRISAT & other, India | n.d. | + | n.d. | n.d. |
| Field-caught | Liao Cheng, China | n.d. | + | n.d. | n.d. |
| *H. punctigera* | | | | | |
| PUNC | Lab Strain | − | − | − | − |
| PNV | Namoi Valley | − | n.d. | − | − |
| Field-caught | Namoi/Gwydir | − | − | n.d. | n.d. |
| Field-caught | Birdsville | − | − | − | − |

"Lab Strains" have been maintained in Canberra for several years
n.d. = not done

TABLE III

Field test kit procedure used for trials in January/February

| Step | Procedure | Incubation time | Comments |
| --- | --- | --- | --- |
| 1 | Squash eggs and/or larvae | | |
| 2 | Add block solution (25 mL) | 1 min | Discard used block solution |
| 3 | Add mAb conjugate solution (25 mL) | 5 min | At the end of the incubation pour conjugate solution back into bottle and re-use up to 4 times. During this incubation prepare wash solution by diluting concentrate 5 fold with tap water |
| 4 | Rinse 3 times (250 ml) | 2 min | |
| 5 | Add substrate (20 ml) and 10 drops of colour developer | ≦1 min | Incubate until control is clearly visible or for 1 min, whichever is shorter |
| 6 | Rinse and score | ≈1 min | |

To save time, 2 or 3 membranes can be processed in parallel by a single operator.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

LIST OF REFERENCES

Beenakkers, A. M. T., H. Chino and J. H. Law (1988). "Lipophorin nomenclature." *Insect Biochemistry* 18(1): 1–2.

Brand, J. A., C. W. Tsang, W. Zhou and S. B. Shukla (1990). "Comparison of particulate 3,3',5,5'-tetramethylbenzidine and 3,3' diaminobenzidine as chromogenic substrates for immunoblot." *Biotechniques* 8(1): 58–60.

Campbell, A. M. (1984). "Monoclonal Antibody Technology." Amsterdam, Elsevier.

Elzen, G. W. Leonard, B. R. Graves, J. B. Burris, E. and Micinski, S. (1992) Resistance to pyrethroid, carbamate, and organophosphate insecticides in field populations of tobacco budworm (Lepidoptera: Noctuidae) in 1990. J. Econ. Entomol 85, 2064–2072.

Engelmann, F., J. Mala and D. Borse (1988). "Juvenile hormone-binding protein and juvenile hormone esterase activity in hemolymph from last-instar nymphs of *Leucophaea maderae*." *Arch. Insect Biochem. Physiol.* 8: 11–23

Fitt, G. P. (1989). "The ecology of Heliothis species in relation to agroecosystems." *Ann. Rev. Entomol.* 34: 17–52.

Forrester, N. W. (1990). "Resistance management in Australian cotton." Fifth Australian Cotton Reference, Broadbeach, Queensland, ACGRA. 361–368.

Goding, J. W. (1983). "Monoclonal Antibodies: Principles and Practice. Production and application of monoclonal antibodies in cell biology, biochemistry and molecular biology." London, Academic Press.

Harlow, E. and D. Lane (188). "Antibodies: A Laboratory Manual." Cold Spring Harbor, Cold Spring Harbor Laboratory Press.

Kawooya, J. K. and J. H. Law (1988). "Role of lipophorin in lipid transport to the insect egg." *The Journal of Biological Chemistry* 263(18): 8748–8753.

Laemmli, U. K. (1970). "Cleavage of Structural proteins during the assembly of the head of bacteriophage T4." *Nature* 227: 680–685.

Lewis, S. A., W. Gu and N. J. Cowan (1987). "Free intermingling of mammalian β-tubulin isotypes among functionally distinct microtubules." *Cell* 49 (May 22, 1987): 539–548.

Lowry, O., N. Rosebrough, A. Farr and R. Randall (1951). "Protein measurement with the Folin phenol reagent." *J.Biol. Chem.* 193: 265–275.

Matthew, W. D. and P. H. Patterson (1983). "The production of a monoclonal antibody that blocks the action of a neurite outgrowth-promoting factor." *CSH symp. Quant. Biol.* 48: 625–631.

Polak, J. and J. Kristek (1988). "Use of horseradish-peroxidase labelled antibodies in ELISA for plant virus detection." *J. Phytopathology* 122: 200–207.

Teakle, R. E. and J. M. Jensen (1985). "*Heliothis punctiger.*" *Handbook of insect rearing.* Amsterdam, Elsevier. 312–322.

Thomas, K. K. and L. I. Gilbert (1968). "Isolation and characterization of the haemolymph lipoproteins of the American silkmoth, *Hyalophora cecropia.*" *Archives of Biochemistry and Biophysics* 127: 512–521.

What is claimed is:

1. An isolated antibody (Ab) which specifically binds to a target lipophorin protein present in both eggs and larvae, or in all life stages, of at least one species or subspecies of insect but not present in at least one other species or subspecies of insect, wherein said isolated antibody is the monoclonal antibody mAb 70.5 (ECACC No. 93012101).

2. The antibody of claim 1 which specifically binds to said lipophorin protein of one species or subspecies of Lepidoptera.

3. The antibody of claim 1 which specifically binds to said lipophorin protein of at least one species or subspecies of Helicoverpa but not at least one other species or subspecies of Heliothis.

4. The antibody of claim 1 which specifically binds to said lipophorin protein of *Helicoverpa armigera* but not *Helicoverpa punctigera.*

5. The antibody of claim 1 wherein said antibody is labeled with a reporter.

6. The antibody of claim 5 wherein said reporter is horseradish peroxidase, glucose oxidase, β-galactosidase, alkaline phosphatase, colloidal gold, latex microbeads or erythrocytes.

7. A method of identifying one or more species or subspecies of insect by determining the reactivity of the monoclonal antibody mAb 70.5 to a target lipophorin protein present in both eggs and larvae, or in all life stages, of at least one species or subspecies of insect, but substantially not present in at least one other species or subspecies of insect, said method comprising contacting a sample of insect material with an effective amount of said mAb 70.5 antibody which specifically binds to said target lipophorin protein of one or more species or subspecies of insect for a time and under conditions sufficient for a complex to form between said mAb 70.5 antibody and said target lipophorin protein, and then detecting said complex.

8. The method of claim 7 wherein said one or more species or subspecies is a Lepidopteran.

9. The method of claim 7 wherein said mAb 70.5 antibody specifically binds to said target lipophorin protein of *Helicoverpa armigera* but not *Helicoverpa punctigera.*

10. The method of claim 7 wherein said mAb 70.5 antibody is labeled with a reporter.

11. The method of claim 10 wherein said reporter is horseradish peroxidase, glucose oxidase, β-galactosidase, alkaline phosphatase, colloidal gold, latex microbeads or erythrocytes.

12. A kit for distinguishing between or identifying one or more species or subspecies of insect from at least one other species or subspecies of insect, said kit comprising in compartmentalized form a first compartment adapted to receive a mAb 70.5 monoclonal antibody which specifically binds to the target lipophorin protein present in both eggs and larvae, or in all life stages, of at least one species or subspecies of insect but not present in at least one other species or subspecies of insect, at least one other compartment adapted to contain a detector means and a support onto which a sample of insect material can be placed.

13. The kit of claim 12 wherein said one or more species or subspecies is a Lepidopteran.

14. The kit of claim 12 wherein said mAb 70.5 monoclonal antibody is conjugated to a reporter.

15. The kit of claim 12 wherein said kit is capable of distinguishing between *Helicoverpa armigera* and *Helicoverpa punctigera.*

16. The kit of claim 12 wherein said support comprises a membrane and said mAb 70.5 antibody is conjugated with horseradish peroxidase, alkaline phosphatase or β-galactosidase; said kit further comprising an enzyme substrate and appropriate buffers.

17. The kit of claim 12 further comprising a purified preparation of a lipophorin or an apolipophorin II or an apolipophorin I from at least one of the species or subspecies of insect to be distinguished or identified, as a positive control.

18. The kit of claim 14 wherein said reporter is horseradish peroxidase, glucose oxidase, β-galactosidase, alkaline phosphatase, colloidal gold, latex microbeads or erythrocytes.

* * * * *